(12) United States Patent
Verlaak et al.

(10) Patent No.: US 12,144,967 B2
(45) Date of Patent: Nov. 19, 2024

(54) MEDICAMENT DELIVERY DEVICE (71) Applicant: Sanofi-Aventis Deutschland GMBH, Frankfurt am Main (DE)

(72) Inventors: Stefan Verlaak, Milan (IT); Ilario Melzi, Milan (IT)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 100 days.

(21) Appl. No.: 16/478,091

(22) PCT Filed: Jan. 22, 2018

(86) PCT No.: PCT/EP2018/051375
§ 371 (c)(1),
(2) Date: Jul. 15, 2019

(87) PCT Pub. No.: WO2018/138022
PCT Pub. Date: Aug. 2, 2018

(65) Prior Publication Data
US 2019/0366002 A1 Dec. 5, 2019

(30) Foreign Application Priority Data
Jan. 24, 2017 (EP) .................................. 17152921

(51) Int. Cl.
*A61M 5/142* (2006.01)
*A61M 5/145* (2006.01)
(Continued)

(52) U.S. Cl.
CPC ...... *A61M 5/2046* (2013.01); *A61M 5/14248* (2013.01); *A61M 5/14586* (2013.01);
(Continued)

(58) Field of Classification Search
CPC ............ A61M 5/2046; A61M 5/14248; A61M 5/14586; A61M 5/155; A61M 2205/587;
(Continued)

(56) References Cited

U.S. PATENT DOCUMENTS 2,842,123 A * 7/1958 Rundhaug ........... A61M 5/1486
604/141
5,718,355 A * 2/1998 Garby ................... G06M 1/083
116/318
(Continued)

FOREIGN PATENT DOCUMENTS

| CN | 87206896 | 6/1988 |
| CN | 2492837 | 5/2002 |

(Continued)

OTHER PUBLICATIONS http://instrumentationtools.com/bourdon-tube-pressure-gauge-working-principle-animation/ (Year: 2015).*
(Continued)

*Primary Examiner* — William R Carpenter
*Assistant Examiner* — William R Frehe
(74) *Attorney, Agent, or Firm* — Fish & Richardson P.C.

(57) ABSTRACT

A medicament delivery device for delivering a liquid medicament, the medicament delivery device comprising: a rigid casing containing a deformable medicament container, the deformable medicament container arranged to contain the liquid medicament; a pressurized gas cartridge connected to the rigid casing via a gas valve; wherein the gas valve is releasable to allow gas flow into the rigid casing to cause an increase in gas pressure in the rigid casing so as to compress the deformable medicament container to displace the liquid medicament.

18 Claims, 4 Drawing Sheets

(51) Int. Cl.
*A61M 5/155* (2006.01)
*A61M 5/20* (2006.01)

(52) U.S. Cl.
CPC ....... *A61M 5/155* (2013.01); *A61M 2205/587* (2013.01); *A61M 2205/8225* (2013.01); *A61M 2205/825* (2013.01)

(58) Field of Classification Search
CPC .... A61M 2205/8225; A61M 2205/825; A61M 2205/8218; A61M 5/1486; A61M 3/0237; A61M 5/14244; A61M 2005/3022; A61M 2005/14513; A61M 2005/14533; A61M 5/14593; A61M 5/148; A61M 5/1483; A61M 5/152; A61M 5/14; A61M 5/142; A61M 2005/14252; A61M 5/145; A61M 5/158; A61M 2005/1585; A61M 2005/1586; A61M 2205/0216; A61M 2205/82; A61M 5/168; A61M 5/16886; A61M 2205/33; A61M 2205/3327; A61M 2205/3331; A61M 2205/3334; A61M 2205/3379; A61M 2205/58; A61M 2205/583
See application file for complete search history.

(56) References Cited

U.S. PATENT DOCUMENTS

| | | | |
|---|---|---|---|
| 5,768,932 | A | 6/1998 | Hahn |
| 6,564,827 | B1 | 5/2003 | Henneborn et al. |
| 2003/0114789 | A1* | 6/2003 | Haar ....................... A61M 5/30 604/69 |
| 2009/0099545 | A1* | 4/2009 | Nilsson ............. A61M 5/14244 604/141 |
| 2010/0087778 | A1 | 4/2010 | Genosar et al. |
| 2010/0206882 | A1 | 8/2010 | Wessels et al. |
| 2011/0011400 | A1* | 1/2011 | Gentner ................ G01F 15/063 136/243 |
| 2012/0132201 | A1* | 5/2012 | Pommereau .......... A61M 15/00 604/131 |
| 2012/0325215 | A1 | 12/2012 | Levenick et al. |
| 2014/0276587 | A1 | 9/2014 | Imran |

FOREIGN PATENT DOCUMENTS

| | | | | |
|---|---|---|---|---|
| CN | | 101806239 | 8/2010 | |
| CN | | 101820935 | 9/2010 | |
| CN | | 201788027 | 4/2011 | |
| DE | | 2731448 | 1/1978 | |
| EP | | 0098893 | 1/1984 | |
| EP | | 0600754 | 6/1994 | |
| EP | | 0600754 A2 * | 6/1994 | ........ A61M 5/14526 |
| EP | | 1527792 | 5/2005 | |
| EP | | 2554196 | 2/2013 | |
| FR | | 2460410 | 1/1981 | |
| JP | | S52-142856 | 10/1977 | |
| JP | | S62-49863 | 3/1987 | |
| JP | | H07-027591 | 5/1995 | |
| JP | | H10-295810 | 11/1998 | |
| JP | | 2016-512123 | 4/2016 | |
| WO | WO 1992/011050 | | 7/1992 | |
| WO | | 2008129549 | 10/2008 | |
| WO | WO 2009/047289 | | 4/2009 | |
| WO | WO 2014/160319 | | 10/2014 | |
| WO | | 2018138022 | 8/2018 | |

OTHER PUBLICATIONS https://gctjaipur.files.wordpress.com/2015/08/electrical-engineering-dictionary-pa-laplantecrc.pdf (Year: 2000) Electrical Engineering Dictionary, Phillip A. Laplante, 2000, p. 243.*
Instrumentation Tools (http://instrumentationtools.com/bourdon-tube-pressure-gauge-working-principle-animation/) (Year: 2015).*
The Electrical Engineering Dictionary by Laplante (https://gctjaipur.files.wordpress.com/2015/08/electrical-engineering-dictionary-pa-laplantecrc.pdf) (Year: 2000).*
Instrumentation Tools (https://instrumentationtools.com/bourdon-tube-pressure-gauge-working-principle-animation/) (Year: 2015).*
The Electrical Engineering Dictionary by Laplante (https://gctjaipur.files.wordpress.com/2015/08/electrical-engineering-dictionary-pa-laplantecrc.pdf) (Year: 2000).*
Electrical Engineering Dictionary by Laplante (Year: 2000).*
PCT International Search Report and Written Opinion issued in International Application No. PCT/EP2018/051375, dated Aug. 2, 2018, 15 pages.
PCT International Preliminary Report on Patentability in International Application No. PCT/EP2018/051375, dated Jul. 30, 2019,10 pages.
Mechanical Parts Design Manual, Continued Edition, Hydraulic transmission and pneumatic transmission, Northeastern Institute of Technology, Matallurgical Industry Press, Dec. 1979, pp. 579-582 (28 pages with English translation).

* cited by examiner

MEDICAMENT DELIVERY DEVICE

CROSS REFERENCE TO RELATED APPLICATIONS

The present application is the national stage entry of International Patent Application No. PCT/EP2018/051375, filed on Jan. 22, 2018, and claims priority to Application No. EP 17152921.7, filed on Jan. 24, 2017, the disclosures of which are incorporated herein by reference.

TECHNICAL FIELD

The present disclosure relates to a device for delivery of medicament to a patient.

BACKGROUND

A variety of diseases exist that require regular treatment by injection of a medicament and such injections can be performed by using injection devices. Various injection devices for delivering injections of medicament are known in the art. Another type of injection pump that is gaining traction is the bolus injector device. Some bolus injector devices are intended to be used with relatively large volumes of medicament, typically at least 1 ml and may be a few ml. Injection of such large volumes of medicament can take some minutes or even hours. Such high capacity bolus injector devices can be called large volume devices (LVDs). Generally such devices are operated by the patients themselves, although they may also be operated by medical personnel.

To use an injector device, such as an LVD, it is first supported on a suitable injection site on a patient's skin. Once installed, injection is initiated by the patient or another person (user). Typically, the initiation is effected by the user operating an electrical switch, which causes a controller to operate the device. Operation includes firstly injecting a needle into the user and then causing the injection of medicament into the user's tissue. Biological medicaments are being increasingly developed which comprise higher viscosity injectable liquids and which are to be administered in larger volumes than long-known liquid medicaments. LVDs for administering such biological medicaments may comprise a pre-filled disposable drug delivery device or, alternatively, a disposable drug delivery device into which a patient or medical personnel must insert a drug cartridge prior to use.

Some medicament delivery devices use bungs and plungers for advancing the liquid medicament during an injection process, but these bungs and plungers may introduce inefficiency during injection due to friction. Furthermore, in these injection arrangements with bungs and plungers, there may be dead volume within medicament containers or syringes due to manufacturing tolerances, which may lead to residual drug even with after fully advancing the bung.

In some patient-operated LVDs, the drug delivery process from start to finish may be a lengthy process and sometimes it is difficult for the patient to determine whether the injection process is complete. Some medicament delivery devices are provided with on-board equipment including light sources and indicator systems for indicating the amount of medicament currently contained within the device. In some of these devices with on-board equipment, batteries are provided so as to power the on-board equipment. However, these devices are often stored for a relatively long time before being used for delivering medicament. A problem is that, during this time of storage, battery corrosion and leakage may occur.

SUMMARY

According to an aspect of the present disclosure, there is provided a medicament delivery device for delivering a liquid medicament comprising: a rigid casing containing a deformable medicament container, the deformable medicament container arranged to contain the liquid medicament; a pressurized gas cartridge connected to the rigid casing via a gas valve; wherein the gas valve is releasable to allow gas flow into the rigid casing to cause an increase in gas pressure in the rigid casing so as to compress the deformable medicament container to displace the liquid medicament.

The medicament delivery device may further comprising an overflow reservoir connected to the rigid casing via a safety valve, wherein the safety valve is configured to allow gas flow into the overflow reservoir when gas pressure in the rigid casing exceed a predetermined threshold.

The medicament delivery device may further comprise a flow detection mechanism in the overflow reservoir.

The flow detection mechanism may comprise a rotation member arranged in the overflow reservoir, wherein the rotation member is configured to be rotated by gas flow in the overflow reservoir.

The rotation member may comprise a plurality of vanes.

The rotation member may be connected to an indicator system.

The indicator system may comprises: a transparent window at the housing; and an indicator member arranged at the rotation member, such that when the rotation member rotates, an outer end of the indicator member moves along the transparent window.

The rotation member may be connected to an energy generating apparatus.

The energy generating apparatus may comprise a dynamo.

The medicament delivery device may further comprise a light source arranged to be powered by the energy generating apparatus.

The deformable medicament container may be in fluid communication with an outlet, the outlet being connected via a fluid path to a needle injection system.

The medicament delivery device may be a bolus injector.

The deformable medicament container may contain a liquid medicament.

According to another aspect of the present disclosure, there is provided a method of operating a medical delivery device, the medical delivery device comprising a rigid casing containing a deformable medicament container arranged to contain a liquid medicament and a pressurized gas cartridge connected to the rigid casing via a gas valve, the method comprising: releasing the gas valve to allow gas flow into the rigid casing to cause an increase in gas pressure in the rigid casing so as to compress the deformable medicament container to displace the liquid medicament.

The medical delivery device may further comprise an overflow reservoir connected to the rigid casing via a safety valve, and the method may further comprise converting motion of gas flow in the overflow reservoir into torque for rotating a rotation member in the overflow reservoir.

These and other aspects of the disclosure will be apparent from and elucidated with reference to the embodiments described hereinafter.

BRIEF DESCRIPTION OF THE FIGURES

Exemplary embodiments of the present disclosure are described with reference to the accompanying drawings, in which.

Reference will now be made in detail to the embodiments, examples of which are illustrated in the accompanying drawings, wherein like reference numerals refer to like elements throughout.

DETAILED DESCRIPTION

A medicament delivery device for delivering a liquid medicament is provided. The medicament delivery device comprises a rigid casing containing a deformable medicament container, the deformable medicament container arranged to contain the liquid medicament; a pressurized gas cartridge connected to the rigid casing via a gas valve; wherein the gas valve is releasable to allow gas flow into the rigid casing to cause an increase in gas pressure in the rigid casing so as to compress the deformable medicament container to displace the liquid medicament.

The medicament delivery device as described avoids the friction associated with bungs and plungers. Furthermore, the dead volume is considerably smaller since the volume inside the deformable medicament container can virtually be reduced to zero whereas in conventional injection arrangements there is usually some residual drug even with after fully advancing the bung due to manufacturing tolerances.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1:
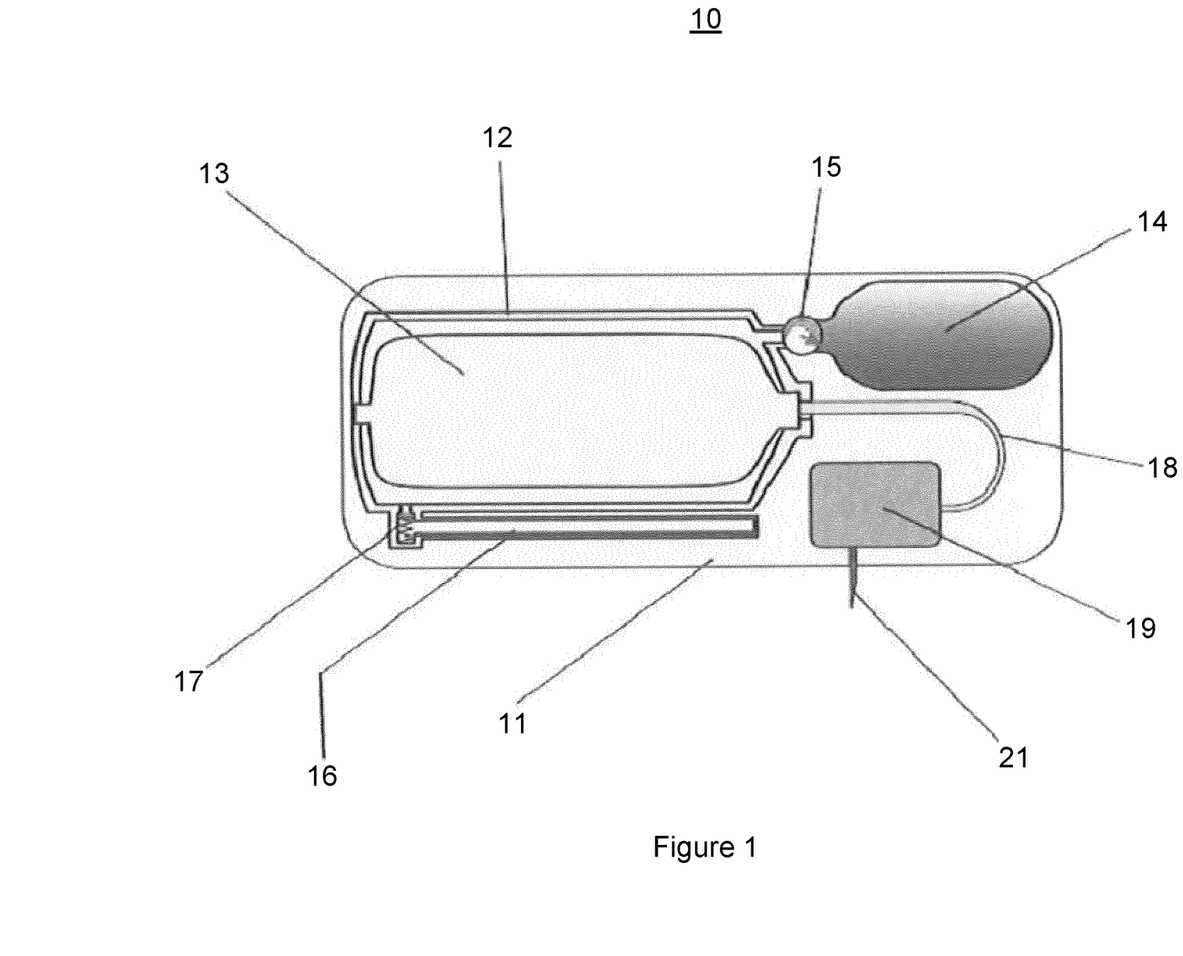
FIG. 1 is a schematic view of a medicament delivery device in an initial state, according to a first embodiment.

FIG. 1 is a schematic view of a medicament delivery device in an initial state, according to a first embodiment. The device is described below in the context of a Large Volume Device (LVD), but it will be appreciated that it could alternatively be another type of bolus injector.

A medicament delivery device 10 according to a first embodiment of the disclosure is shown in FIG. 1. The medicament delivery device 10 can either be a stationary or a portable device. The medicament delivery device 10 comprises a housing 11 containing a rigid casing 12 connected to a pressurized gas cartridge 14 via a gas valve 15. The rigid casing 12 may be made of metal or hard plastic, and it will be appreciated that the rigid casing may be made of other materials that provide the required rigidity of the rigid casing 12.

The pressurized gas cartridge 14 in this embodiment has a volume of 5 ml and contains nitrogen gas pressurized at 1,000 Pa. The gas valve 15 in the present embodiment is controlled by an actuator (not shown in FIG. 1). When the actuator is actuated, the gas valve 15 is arranged to release to as to allow gas flow from the pressurized gas cartridge 14 into the rigid casing 12. In this embodiment, the gas valve 15 is a one-way valve that only allows gas to flow through in one direction, i.e. from the pressurized gas cartridge 14 to the rigid casing 12.

The rigid casing 12 contains a deformable medicament container 13 which in the initial state is filled with liquid medicament. The deformable medicament container 13 may be made of plastic, e.g. polyvinyl chloride (PVC) or polyethylene. In the present embodiment, the deformable medicament container 13 is attached at a side of the rigid casing 12 opposite the outlet of the medicament container 13, in order to ensure a precise folding of the deformable medicament container 13. Specifically, as shown in this embodiment, the rigid casing 12 has an elongate shape and the deformable medicament container 13 is held at a front end in the region of the outlet of the medicament container 13 where it is sealed against the rigid casing 12 and at a back end opposite the outlet of the medicament container 13. In the initial state, the deformable medicament container 13 with the liquid medicament essentially fills the entire volume of the rigid casing 12.

The deformable medicament container 13 comprises an outlet through which medicament can be displaced. The outlet of the deformable medicament container 13 is connected to a needle injection system 19 through a fluid path 18. In other words, an end of the fluid path 18 is connected to the outlet of the medicament container 13 while another end of the fluid path 18 is connected to a needle injection system 19. The needle injection system 19 includes a hollow injection needle 21 through which medicament can be displaced when the deformable medicament container 13 is compressed.

The rigid casing 12 is Tillable by gas for displacing the deformable medicament container 13 and thus the liquid medicament inside. Therefore, when the gas valve 15 releases to allow gas flow into the rigid casing 12, the increase gas pressure exerts a compressive force on the deformable medicament container 13 so as to displace the liquid medicament contained within through its outlet.

The medicament delivery device 10 further comprises an overflow reservoir 16. The overflow reservoir 16 is connected to the rigid casing 12 via a safety valve 17. The safety valve 17 is configured such that when a gas pressure within the rigid casing 12 exceeds a predetermined threshold, the safety valve 17 releases so as to allow gas flow into the overflow reservoir. Hence, safety can be ensured by preventing a scenario in which the gas pressure within the rigid casing reaches dangerously high levels. In this embodiment, the safety valve 17 is a pressure relief valve (PRV) which is set to open at a predetermined set pressure to protect the rigid casing 12 from being subjected to pressures that exceed its design limit.

Figure 2:
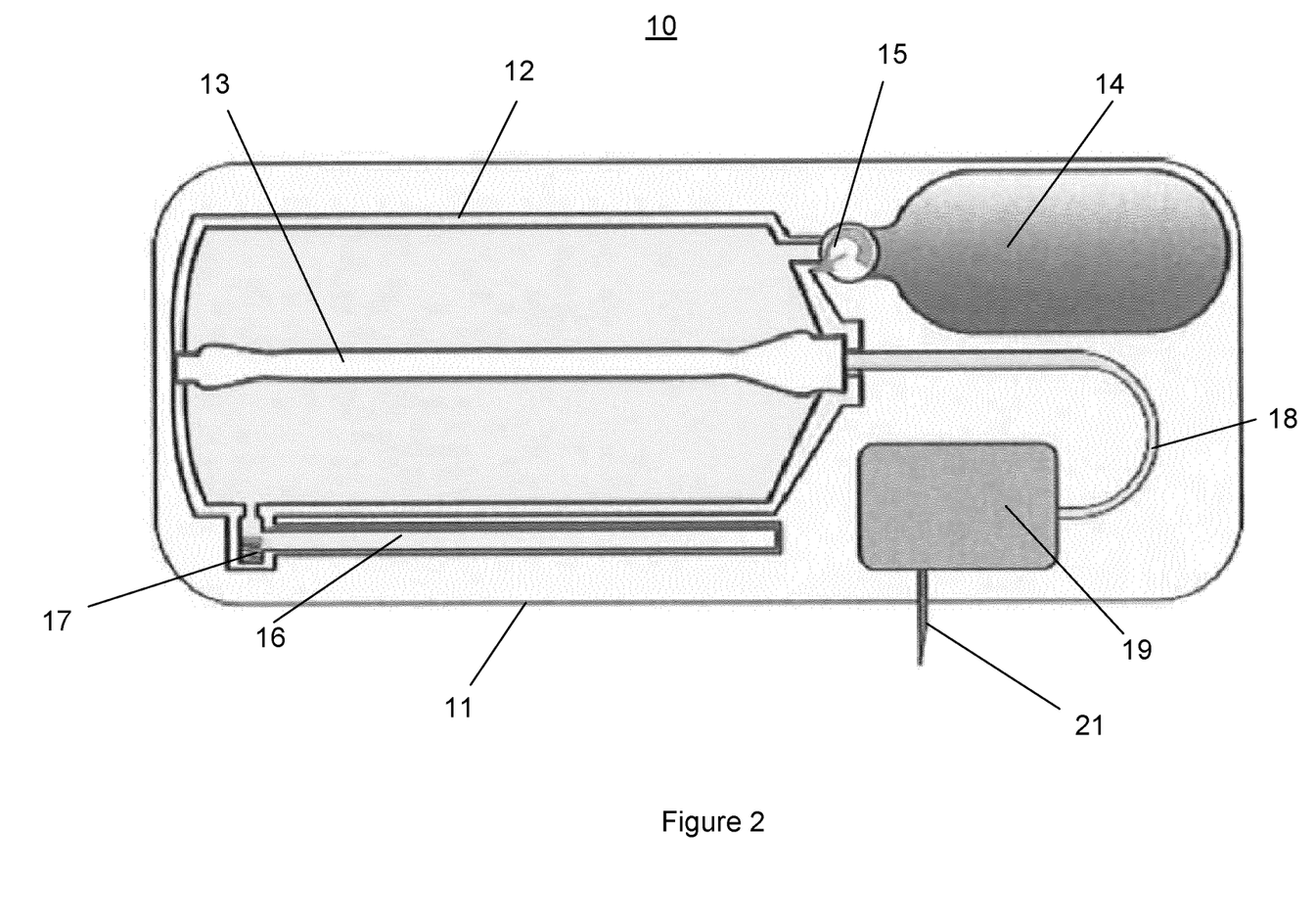
FIG. 2 is a schematic view of a medicament delivery device in a final state, according to the first embodiment.

FIG. 2 is a schematic view of a medicament delivery device in a final state, according to the first embodiment.

The medicament delivery device 10 as shown in FIG. 2 is in the final state, when the actuator which is arranged to control the gas valve 15 is actuated to allow gas flow from the pressurized gas cartridge 14 in the rigid casing 12. In the final state, the whole content of the deformable medicament container 13 may be forced out of the outlet by entirely filling the rigid casing 12 with gas and thereby fully compressing the deformable medicament container 13.

Due to the rigidness of the rigid casing 12, when gas flows into the rigid casing 12 from the pressurized gas cartridge 14, the increased gas pressure exerts a compressive force on the deformable medicament container 13 arranged within the rigid casing 12 to compress the deformable medicament container 13. The liquid medicament contained within the deformable medicament container 13 is displaced through its outlet, through the fluid path, and to the needle injection system 19 to be injected to an injection site.

Once all the content within the deformable medicament container 13 has been displaced, the gas pressure within the rigid casing 12 will continue to increase due to the continued gas flow from the pressurized gas cartridge 14. When the gas pressure within the rigid casing exceeds the predetermined threshold, the safety valve 17 would release to allow gas flow into the overflow reservoir 16. This gas flow from the rigid casing 12 causes the gas pressure in the rigid casing 12 to decrease and therefore damage to the rigid casing 12 due to high gas pressure can be prevented.

Figure 3A:
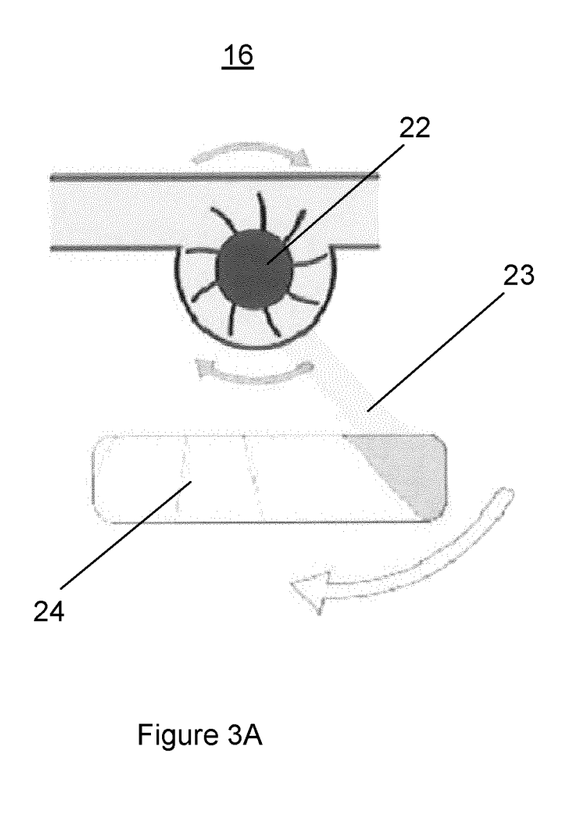
FIG. 3A is a schematic view of part of the medicament delivery device in a first state, according to a second embodiment.
Figure 3B:
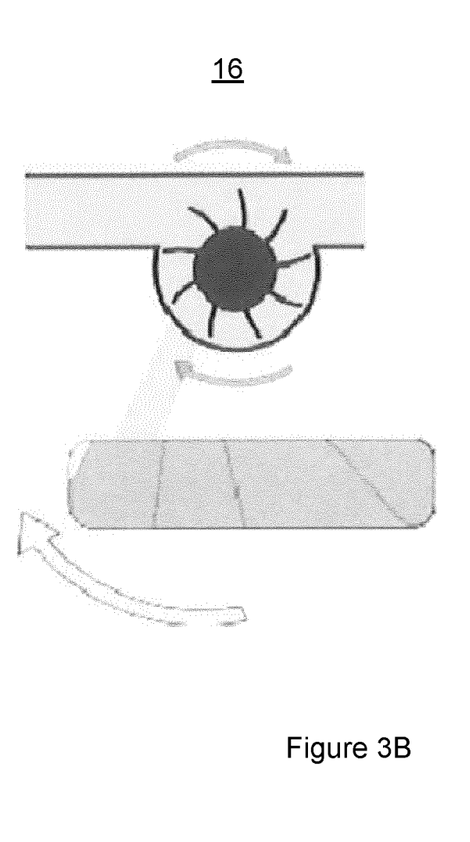
FIG. 3B is a schematic view of part of the medicament delivery device in a second state, according to the second embodiment.

FIG. 3A is a schematic view of part of a medicament delivery device in a first state, according to a second embodiment, and FIG. 3B is a schematic view of part of the medicament delivery device in a second state, according to the second embodiment. Specifically, FIGS. 3A and 3B show part of the overflow reservoir 26 of the medicament delivery device respectively before completion of the injection process (i.e. the first state), and after completion of the injection process (i.e. the second state).

The medicament delivery device of the second embodiment is similar to the medicament delivery device 10 of the first embodiment, with the addition of a rotation member 22 arranged in the overflow reservoir 16, the rotation member 22 being connected to an indicator system comprising an indicator member 23 and a transparent window 24. The transparent window 24 in this embodiment is positioned at the housing 11 to allow a user to determine an orientation of the indicator member.

In this embodiment, the rotation member 22 is considered as a flow detection mechanism. The rotation member 22 is arranged in the overflow reservoir 16 and is in particular configured to rotate in a single direction (clockwise as shown in FIGS. 3A and 3B) when gas flows into the overflow reservoir 16 from the rigid casing 12. In other words, motion of gas flow in the overflow reservoir 16 is converted into torque for rotating the rotation member 22.

In this embodiment, the indicator member 23 of the indicator system is a narrow elongate member arranged at a surface of the rotation member 22 such that it extends from a center of the rotation member 22 outwards. The indicator member 23 is fixedly attached to the rotation member 22 such that as the rotation member 22 rotates, an outer end of the indicator member 23 moves along the transparent window 24 from a first position to a second position. The first position corresponds to the first state in which the injection process is not complete, and the second position corresponds to the second state in which the injection process is complete.

A first end of the transparent window 24 represents when the deformable medicament container 13 is non-empty, and a second end of the transparent window 24 represents when the deformable medicament container 13 is empty. Therefore, when the outer end of the indicator member 23 moves along the transparent window 24 from one end to another, a user is able to determine that the injection process is complete.

When the actuator (not shown in the drawing) is actuated to release the gas valve 15, the rigid casing 12 is gradually filled with gas and thus the gas pressure within the rigid casing 12 continues to increase. This increasing gas pressure exerts a compressive force on the deformable medicament container 13 so as to displace the liquid medicament contained within through its outlet.

Once all the content within the deformable medicament container 13 has been displaced, the gas pressure within the rigid casing 12 will continue to increase due to the continued gas flow from the pressurized gas cartridge 14. When the gas pressure within the rigid casing exceeds the predetermined threshold, the safety valve 17 would release to allow gas flow into the overflow reservoir 16.

The gas flow into the overflow reservoir 16 causes a rotation of the rotation member 22 in a single direction, which in turn causes the outer end of the indicator member 23 to sweep along the transparent window 24 from one end to another. This is illustrated in FIG. 3A and FIG. 3B, which respectively show the outer end of the indicator member 23 in the first position (FIG. 3A) and in the second position (FIG. 3B). Hence, when the outer end of the indicator member 23 moves from one end to another along the transparent window 24, the user is able to determine when the deformable medicament container 13 is empty and when the injection process is complete by checking the orientation of the indicator member 23.

Figure 4:
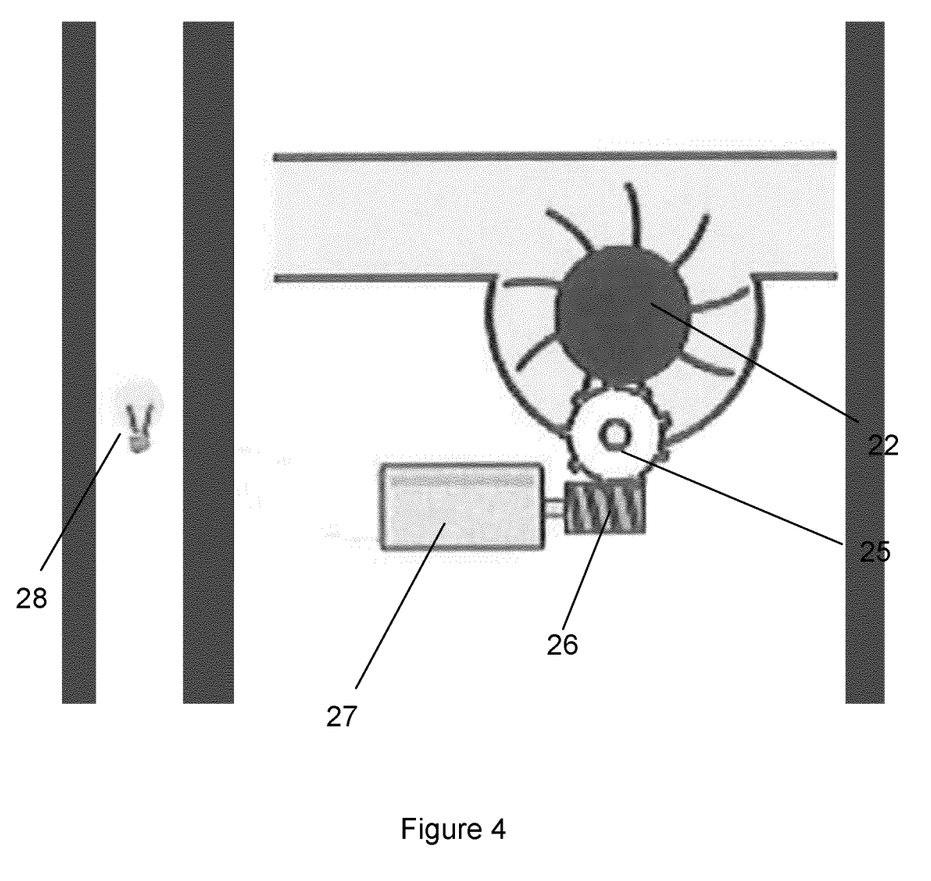
FIG. 4 is a schematic view of a medicament delivery device according to a third embodiment.

FIG. 4 is a schematic view of part of a medicament delivery device according to a third embodiment.

The medicament delivery device of the third embodiment is similar to the medicament delivery device the first embodiment, with the addition of a rotation member 22, a pinion gear (not shown in FIG. 4), a worm wheel 25, a worm screw 26, an energy generating apparatus 27, and a light source 28.

In this embodiment, the rotation member 22 is considered as part of a flow detection mechanism. The rotation member 22 is arranged in the overflow reservoir 16 and is in particular configured to rotate in a single when gas flows into the overflow reservoir 16 from the rigid casing 12. In other words, motion of gas flow in the overflow reservoir 16 is converted into torque for rotating the rotation member 22.

As shown in FIG. 4, in this embodiment the rotation member 22 comprises a plurality of vanes and is fixedly attached to a pinion gear (not shown in FIG. 4) configured to mesh with the worm wheel 25. The worm wheel 25 in this embodiment forms a worm drive arrangement with a worm screw 26. Specifically, the worm wheel 25 comprises a plurality of teeth which mesh with a threaded arrangement on an outer surface of the worm screw 26. In this worm drive arrangement, rotary motion is transmitted through a 90° angle. In other words, the rotary motion of the worm wheel 25 in a first axis causes a rotary motion of the worm screw 26 in a second axis, the first axis being perpendicular to the second axis.

The worm screw 26 is mechanically connected to the energy generating apparatus 27. In this embodiment, the energy generating apparatus 27 comprises a dynamo which is configured to convert mechanical rotation into a direct electric current.

Although not shown in the drawing, the energy generating apparatus 27 is electrically connected to a light source 28, which in this embodiment is a light bulb. Therefore, as energy generating apparatus 27 converts mechanical rotation of the worm screw 26, the light source 28 is powered.

When the actuator (not shown in the drawing) is actuated to release the gas valve 15, the rigid casing 12 is gradually filled with gas and thus the gas pressure within the rigid casing 12 continues to increase. This increasing gas pressure exerts a compressive force on the deformable medicament container 13 so as to displace the liquid medicament contained within through its outlet.

Once all the content within the deformable medicament container 13 has been displaced, the gas pressure within the rigid casing 12 will continue to increase due to the continued gas flow from the pressurized gas cartridge 14. When the gas pressure within the rigid casing exceeds the predetermined threshold, the safety valve 17 would release to allow gas flow into the overflow reservoir 16.

The gas flow into the overflow reservoir 16 causes a rotation of the rotation member 22 in a single direction. Due to the attachment between the rotation member 22 and the pinion gear (not shown in FIG. 4), the pinion gear rotates together with the rotation member 22 and meshes with the worm wheel 25 which in turn meshes with the worm screw 26 so as to transmit rotary motion through a 90° angle. As the worm screw 26 rotates, a current is generated by the energy generating apparatus 27 to which the worm screw 26 is connected to. In the present embodiment, this generated energy is used to power the light source 31. Thus, the light source 31 can be used for indicating that the injection process is complete.

In alternative embodiments, the medicament delivery device may be a pen injector instead of a bolus injector.

In alternative embodiments, the energy generating apparatus may be electrically connected to an energy storing apparatus, such as a capacitor, instead of being connected directly to a light source. In these alternative embodiments, the energy (direct electric current) generated at the energy generating apparatus may be stored at the energy storing apparatus and may be used subsequently for powering on-board equipment at the device.

In alternative embodiments, the deformable medicament container may be made of other material which would allow the medicament container to be compressed and/or folded under gas pressure.

In alternative embodiments, the gas valve at which the pressurized gas cartridge and the rigid casing are connected may be controllable by a different element in the device. For example, the gas valve may be controlled by a control device (e.g. a dial) so as to control and adjust a gas flow rate from the pressurized gas cartridge into the rigid casing. Also, in alternative embodiments, other types of valves (e.g. a diaphragm valve, a pinch valve, etc.) may be used instead of a one-way valve as the gas valve.

In alternative embodiments, other types of gases (e.g. air, carbon dioxide, oxygen, etc.) may be used as the gas contained in the pressurized gas cartridge, instead of nitrogen. Also, in alternative embodiments, the gas contained in the pressurized gas cartridge may be pressurized in a different gas pressure value.

In alternative embodiments, the size and/or dimension of the pressurized gas cartridge may be adapted according to design requirements.

In alternative embodiments, the safety valve at which the overflow reservoir and the rigid casing are connected may be a pressure safety valve (PSV) instead of a pressure relief valve (PRV). Also, in alternative embodiments, other types of valves may be used as the safety valve, instead of a pressure relief valve.

In alternative embodiments, the rotation member may be replaced by other types of flow detection mechanisms in the overflow reservoir. In these alternative embodiments, the flow detection mechanism may comprise at least one of a: an Archimedes screw member, an ultrasonic detection device, an electromagnetic transmission detection device. Also, in these alternative embodiments, the flow detection mechanism may be connected to the indicator system or the energy generating apparatus. For example, in an alternative embodiment with a flow detection mechanism comprising an Archimedes screw member, the Archimedes screw member may be mechanically connected to an energy generating apparatus so as to generate direct current when the Archimedes screw member rotates due to gas flow in the overflow reservoir.

In alternative embodiments, the indicator member and the scale of the indicator system may adopt other shapes and configurations. For example, the indicator member in an alternative embodiment may be a fan-shaped member arranged at a surface of the rotation member such that it extends from a center of the rotation member outwards, and the scale may be an arc-shaped aperture of a flat covering member arranged on top of the indicator member. The indicator member may be fixedly attached to the rotation member such that as the rotation member rotates, the indicator member rotates so as to cover the arc-shaped aperture (i.e. the scale). In other alternative embodiments, a linear scale may be used instead.

Although claims have been formulated in this application to particular combinations of features, it should be understood that the scope of the disclosure also includes any novel features or any novel combinations of features disclosed herein either explicitly or implicitly or any generalization thereof, whether or not it relates to the same disclosure as presently claimed in any claim and whether or not it mitigates any or all of the same technical problems as does the present disclosure. The applicant hereby gives notice that new claims may be formulated to such features and/or combinations of features during the prosecution of the present application or of any further application derived therefrom.

Those skilled in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A large volume device (LVD) configured to deliver a liquid medicament to a patient, the LVD comprising:
 a housing configured to adhere to the patient's skin during the delivery of the liquid medicament to the patient, the housing containing:
  a needle injection system configured to insert a needle into the patient at the housing;
  a rigid casing containing a deformable medicament container that is configured to contain the liquid medicament in an initial state of the LVD;

a pressurized gas cartridge;

an overflow reservoir; and a flow detection mechanism in the overflow reservoir, wherein the deformable medicament container is in fluid communication with an outlet, and wherein the outlet is connected via a fluid path to the needle;

wherein the pressurized gas cartridge is connected to the rigid casing via a gas valve;

wherein the overflow reservoir is connected to the rigid casing via a safety valve, the safety valve having an open state and a closed state, and the overflow reservoir arranged to receive gas from the rigid casing when the safety valve is in the open state;

wherein the gas valve is releasable to allow a flow of the gas into the rigid casing to cause an increase in a pressure of the gas in the rigid casing so as to compress the deformable medicament container to displace the liquid medicament, and wherein the safety valve is configured to transition from the closed state to the open state to allow the flow of the gas from the rigid casing into the overflow reservoir when the pressure of the gas in the rigid casing exceeds a predetermined threshold corresponding to when an injection process is complete; and wherein the flow detection mechanism comprises a rotation member arranged in the overflow reservoir that is configured to be rotated by the flow of the gas in the overflow reservoir to indicate when the injection process is complete, wherein the rotation member is connected to an indicator system comprising an indicator member, and wherein the rotation member is arranged to move the indicator member from a first position corresponding to a first state in which the injection process is not complete to a second position corresponding to a second state in which the injection process is complete.

2. The LVD of claim 1, wherein the rotation member comprises a plurality of vanes.

3. The LVD of claim 1, wherein the indicator system further comprises a transparent window at the housing, and wherein the indicator member is arranged at the rotation member, such that when the rotation member rotates, an outer end of the indicator member moves along the transparent window.

4. The LVD of claim 1, wherein the rotation member is connected to an energy generating apparatus.

5. The LVD of claim 4, wherein the energy generating apparatus comprises a dynamo.

6. The LVD of claim 4, further comprising a light source arranged to be powered by the energy generating apparatus.

7. The LVD of claim 1, wherein the LVD is a bolus injector.

8. The LVD of claim 1, wherein the deformable medicament container contains the liquid medicament.

9. The LVD of claim 1, wherein the LVD is configured to adhere to the patient's skin for about 5 minutes to about 120 minutes.

10. The LVD of claim 9, wherein the LVD is configured to deliver a volume of about 2 ml to about 10 ml of the liquid medicament during the injection process.

11. The LVD of claim 9, wherein the LVD is configured to inject the liquid medicament over a time period of about 10 minutes to about 60 minutes.

12. The LVD of claim 1, wherein the LVD is configured to retract the needle.

13. A method of operating a large volume device (LVD) configured to deliver a liquid medicament to a patient, the LVD comprising:

a housing configured to adhere to the patient's skin during the delivery of the liquid medicament to the patient, the housing containing:

a needle injection system configured to insert a needle into the patient at the housing;

a rigid casing containing a deformable medicament container that is configured to contain the liquid medicament in an initial state of the LVD;

a pressurized gas cartridge;

an overflow reservoir; and a flow detection mechanism in the overflow reservoir, wherein the deformable medicament container is in fluid communication with an outlet, and wherein the outlet is connected via a fluid path to the needle;

wherein the pressurized gas cartridge is connected to the rigid casing via a gas valve;

wherein the overflow reservoir is connected to the rigid casing via a safety valve, the safety valve having an open state and a closed state, and the overflow reservoir arranged to receive gas from the rigid casing when the safety valve is in the open state;

wherein the method comprises releasing the gas valve to allow the gas to flow into the rigid casing to increase a pressure of the gas in the rigid casing so as to compress the deformable medicament container to displace the liquid medicament, and wherein the safety valve is configured to transition from the closed state to the open state to allow the gas from the rigid casing into the overflow reservoir when the pressure of the gas in the rigid casing exceeds a predetermined threshold corresponding to when an injection process is complete; and wherein the flow detection mechanism comprises a rotation member arranged in the overflow reservoir that is configured to be rotated by the flow of the gas in the overflow reservoir to indicate when the injection process is complete, wherein the rotation member is connected to an indicator system comprising an indicator member, and wherein the rotation member is arranged to move the indicator member from a first position corresponding to a first state in which the injection process is not complete to a second position corresponding to a second state in which the injection process is complete.

14. The method of claim 13, further comprising converting motion of the flow of the gas in the overflow reservoir into a torque for rotating the rotation member in the overflow reservoir.

15. The method of claim 13, wherein the LVD is configured to adhere to the patient's skin for about 5 minutes to about 120 minutes.

16. The method of claim 15, wherein the LVD is configured to deliver a volume of about 2 ml to about 10 ml of the liquid medicament during the injection process.

17. The method of claim 15, wherein the LVD is configured to inject the liquid medicament over a time period of about 10 minutes to about 60 minutes.

18. The method of claim 13, wherein the LVD is configured to retract the needle.

* * * * *